(12) United States Patent
Garrett

(10) Patent No.: US 6,387,360 B1
(45) Date of Patent: May 14, 2002

(54) ANTI-JAUNDICE COMPOSITION FOR CORPSES AND METHOD

(76) Inventor: Kurt Anthony Garrett, 8220 Hobhouse Cir., Raleigh, NC (US) 27615

( * ) Notice: Subject to any disclaimer, the term of this patent is extended or adjusted under 35 U.S.C. 154(b) by 0 days.

(21) Appl. No.: 09/723,826

(22) Filed: Nov. 28, 2000

(51) Int. Cl.$^7$ .............................. A01N 1/00; A61K 7/09
(52) U.S. Cl. ..................... 424/75; 424/70.2; 424/78.02; 424/401; 514/822
(58) Field of Search ....................... 424/75, 401, 78.02, 424/70.2; 514/822

(56) References Cited

U.S. PATENT DOCUMENTS

| | | | |
|---|---|---|---|
| 2,333,182 A | * 11/1943 | Jones et al. ..................... 27/21 |
| 3,774,927 A | * 11/1973 | Duncan .......................... 27/22 |
| 3,997,656 A | * 12/1976 | Wertlake et al. ................ 424/3 |
| 4,404,181 A | * 9/1983 | Mauthner ....................... 424/3 |
| 5,432,056 A | * 7/1995 | Hartman et al. ............ 435/7.21 |
| 5,948,397 A | * 9/1999 | Van Kersen et al. .......... 424/75 |
| 6,072,086 A | * 6/2000 | James et al. ................ 568/449 |

* cited by examiner

Primary Examiner—Thurman K. Page
Assistant Examiner—Charesse L. Evans
(74) Attorney, Agent, or Firm—Glasgow Law Firm; JiNan Glasgow

(57) ABSTRACT

An anti-jaundice composition for providing coloration to a corpse, comprising a bleaching agent, a coloring agent, and a fixing agent, mixed and stored at room temperature, and administered internally to a corpse for providing uniform, controlled coloration of the skin and tissue and for preventing tissue degradation. The invention is also directed to a method for providing an anti-jaundice composition for providing coloration to a corpse.

19 Claims, No Drawings

ANTI-JAUNDICE COMPOSITION FOR CORPSES AND METHOD

BACKGROUND OF THE INVENTION (1) Field of the Invention

The present invention relates generally to a composition and method for providing coloration to corpses and, more particularly, to an anti-jaundice composition for corpses and method for administering the same.

(2) Description of the Prior Art

The top 3 problems in the mortuary industry include airborne tuberculosis, ¾ face repair, and jaundice. Jaundice is the yellow-green discoloration of the skin of corpses due to degradation of body tissues and fluids. Embalming is used to try to prevent accelerated degradation of the tissues and fluids, and thus jaundice.

Embalming should be performed as soon as possible, or else the blood enzymes may cause premature degradation of the corpse. Generally, the body should be washed thoroughly with soap and water. Next, at least one vein is opened to drain the blood from the body, (usually the femoral and the axillary vein). Massaging of the body in the direction of the heart helps to break up any clots that may have formed. Four to six pints of embalming fluid are added, then the blood is drained away from the vein. Inadequate drainage can lead to premature decomposition.

The modem method of embalming is defined as the disinfection of preservation of the dead human body. It is performed for three reasons; disinfection, preservation, and restoration.

The primary purpose of embalming is disinfection. While some pathogens die soon after the death of the host, it is also true that many dangerous organisms have the ability to survive for long periods of time in dead tissues. Persons coming in direct contact with the unembalmed body can become infected as well as there being the possibility of flies or other agents transferring pathogens to humans and infecting them. The second purpose of embalming is preservation. The prevention of putrefaction and decomposition allows the disposition of the remains by burial, cremation, or entombment to take place without the odors or other unpleasantness that would accompany an uncared for remains.

The third purpose of embalming is restoration. Returning the body to a life-like appearance has received many critics, but the custom of viewing the body after death in a state of rest remains a practice of proven psychological worth.

The modern embalming process is designed to retard tissue decomposition for the period of time necessary for disposition as arranged for by the family of the deceased. Under favorable conditions however, modern embalming has been shown to be able to keep a body intact for decades.

Rather than prevent the body from returning to its natural elements, embalming allows the body to decompose by oxidation and dissolution rather than by putrefaction or rotting.

Embalming is accomplished by a chemical "fixation" of the cell protein. Formaldehyde basically reacts with the soluble albumins in the cell and converts them to albuminoids or gels. At the same time, the bacteria are destroyed, thus halting or at least delaying decomposition. Once embalming is properly completed, the body can only be attacked by air-borne bacteria and molds that can eventually destroy the body exposed to air if sufficient moisture is present to support bacterial and mold growth.

In modern embalming then, an embalming fluid that is both a disinfectant and a preservative is injected into the circulatory system of the body by an electric pump while the blood is forced out of the body and disposed of. In effect, the blood is replaced with a disinfectant and preservative solution.

The normal steps to preparation of the body consists of:

The body is placed in a proper position on the embalming table with the arms laid over the stomach.

The body is washed and disinfected.

The face is shaved as necessary.

The eyes are closed. This is usually accomplished with a small curved plastic disc called an "eye cap" placed under the eyelid. Perforations in the cap help hold the eye lid in place.

The mouth is closed. This is usually accomplished by the placing of a specially designed "tack" in the upper and lower jaw. Each tack has a fine wire attached. By twisting the two wires together, the jaw is thus closed and the lips are set to the natural lip line using a cream to retain the proper position and to prevent dehydration.

The embalming solution is prepared. The modern embalming machine consists of a 2–3 gallon reservoir and an electric pump. A solution of approximately 8 ounces of fluid to 1 gallon water is prepared.

An incision is made over the carotid artery (where the neck meets the shoulder) or over the femoral artery (in the leg at the groin). The artery and vein are located and isolated.

A tube which is attached to the machine is inserted into the artery. A slightly larger tube is placed into the accompanying vein. This tube is attached to a hose to the sewer system.

The fluid is injected into the artery under pressure by the embalming machine. As the blood is displaced by the fluid going in, it is forced out of the vein tube and disposed of. The pressure forces the embalming fluid into the capillaries and eventually to the cells of the body. After approximately 3 gallons of solution are injected into the body, the blood has thinned and the fluid coming through the vein tube is mostly embalming fluid.

The tubes are removed and the incision sutured.

The abdominal cavity is treated by the use of a hollow tube called a trocar that is used to aspirate gases and liquid contents under suction. A preservative chemical is introduced.

The body is again washed and cream is placed on the hands and face to prevent dehydration.

The hair is shampooed and the finger nails cleaned.

The body is covered with a sheet awaiting dressing and placement in the casket.

Cosmetics are later applied to replace the natural color removed by the embalming process, much of which is created by blood in facial capillaries that is no longer present. In the case of women, cosmetics used in life may also be used to recreate the "look" the person had during life. The hair is combed or set.

In an unrelated art area, erythrosin is used for self-tanning products to provide better coloration in living human beings; however, this is applied externally and can cause problems of uneven coloration, ecg., streaking, blotchiness. It is also inconvenient to apply in that the person applying must wear protection. It also stains everything. It is a difficult form to use. It is even more difficult to apply to a corpse because body position is difficult. Once again, the external application over discolored skin due to jaundice can cause problems of uneven coloration, streaking, blotchiness, unattractive color, and the like. Also, give an unhealthy, orange appearance when applied to healthy living skin. It is not appropraiate to inject in living humans because fo the likelihood of adverse health reactions.

However, it is desirable in the embalming practice to give the corpse a more realistic and attractive appearance. Currently, coloration control in corpses is problematic, particularly because of skin discoloration due to jaundice. External coloration applications, e.g. makeup, powder, and the like, do not successfully create a realistic and attractive appearance when applied superficially to correct the problem of skin discoloration due to jaundice.

Embalming fluid typically includes a water-based solution having preservatives. By way of example, Nu-Leco, a commercially available product manufactured by ESCO, is for preserving the viscera in autopsied cases and treating burns, cancers, sores, jaundice, hepatities and a variety of other difficult conditions. Nu-Leco is the successor to Esco-Leco which became so well known and trusted by thousands of experienced Embalmers. Its general purpose is to properly treat conditions for which a formaldehyde fluid is unsuited because of its chemical reaction, etc. Nu-Leco is harmless to true porcelain enamel, metals, or the living skin. Nu-Leco may be used for cavity preparation, or as an arterial fluid under special conditions as directed. Like other commercially available embalming products, the exact formulations of the Nu-Leco are considered proprietary.

Thus there remains a need for an anti-jaundice product that provides a uniform, improved skin coloration for corpses.

SUMMARY OF THE INVENTION

One object of the present invention is to provide an anti-jaundice product that provides a uniform, improved skin coloration for corpses.

Another object of the present invention is to provide an anti-jaundice product that provides a uniform, improved skin coloration for corpses that is convenient to apply.

Thus, one aspect of the present invention is to provide an anti-jaundice product that provides a uniform, improved skin coloration for corpses.

Another aspect of the present invention is to provide an antijaundice product that provides a uniform, improved skin coloration for corpses that is introduced intravenously to the corpse.

Still another aspect of the present invention is to provide an anti-jaundice product that provides a uniformn, improved skin coloration for corpses that is produced and stored a room temperature.

DETAILED DESCRIPTION OF A PREFERRED EMBODIMENT

The present invention relates to a composition comprising a bleaching agent, a coloring agent, and a fixing agent. The bleaching agent reduces and eliminates discoloration in the skin and body due to jaundice. The coloring agent introduces a predetermined, controlled and uniform coloration to the skin, previously discolored due to jaundice. The fixing agent reduces and eliminates microbial or self-degradation of the body and skin due to microbial or self-discoloration in the skin and body due to jaundice.

What is meant by bleaching agent is a chemical agent capable of removing pigmentation and discoloration, particularly of the skin. By way of example, and not of limitation, examples of bleaching agents include peroxides, including benzoyl peroxide, hydrogen peroxide, and reasonable equivalents, chlorine bleach, and the like. In the preferred embodiment, benzoyl peroxide is used as the bleaching agent.

What is meant by coloring agent is a chemical agent capable of producing or inducing the artificial skin coloration and is introduced intravenously. By way of example, and not of limitation, examples of coloring agents include erythrosine, 1,3,4-trihydroxy-2-butanone (i.e., erythrulose), alloxan, methyl glyoxal, ethoxydiglycol, glyceraldehyde, various indoles and imidazoles and their derivatives, pigmentation agents such as methoxselen and trioxselan, and .alpha.-hydroxy ketones and aldehydes, e.g. 1,3-dihydroxyacetone (i.e., dihydroxyacetone). In the preferred embodiment, erythrosine is used as the coloring agent.

What is meant by fixing agent is a chemical agent capable of stabilizing tissues to prevent autolysis and microbial degradation of the tissues, particularly of the skin. By way of example, and not of limitation, examples of fixing agents include formaldehyde, phenol, methanol, and reasonable equivalents, and the like, separately or in combination. In the preferred embodiment, formaldehyde, phenol, and methanol in combination are used as the fixing agent.

In the preferred embodiment, the anti-jaundice composition is administered intravenously to the corpse, preferably by injection. The injection may be intravenous, intraarterial, intramuscular, or subcutaneous. The injection may be locally administered to produce a localized bleaching and coloration effect, or may be administered systemically to the entire corpse. The anti-jaundice can be stored at room temperature for a limited time.

Following is an example of the preferred embodiment anti-jaundice composition, provided by way of example and not of limitation. The weight percentage of the ingredients of the anti-jaundice composition of this Example 1 are set forth below in Table 1.

TABLE 1

| INGREDIENTS | Volume (%) |
| --- | --- |
| Step A | |
| WATER | 12.5 |
| METHANOL | 25.0 |
| PHENOL | 12.5 |
| FORMALDEHYDE | 50.0 |
| Step B | |
| ERYTHROSIN | to color specification[1] |
| Step C | |
| BENZOYL PEROXIDE | to saturation[2] |

[1]between about 5 mg to about 5 grams erythrosin/gallon
[2]between about 10 to about 30 g/gallon of benzoyl peroxide, crystalline form The water, methanol, phenol, and formaldehyde of Step A are mixed at room temperature to form the intermediate mixture. The intermediate mixture is maintained at room temperature. Then in Step B, the erythrosin is added to the intermediate mixture and dissolved, also at room temperature, to form a secondary mixture. The secondary mixture should have an amber color, similar to the color of gasoline. The amount of erythrosine to add can be varied, according to the amount of coloration desired, between about 5 mg to about 5 grams erythrosin/gallon. If the mixture becomes pink, then too much erythrosin has been added, and may excessively color the corpse; however, this may vary due to initial skin coloration of the corpse, i.e., darker skin tones may require less coloration and therefore less erythrosin. Notably, the secondary mixture resulting from Step A and Step B both having been completed, is presently commercially available from CSMO, Inc. of Raleigh, N.C. under the label CS-30 as embalming fluid that provides some advantages over prior art embalming fluids. Upon completion of Step B, then benzoyl peroxide is added in a Step C, preferably in crystalline form although possible to add as a liquid, to the secondary mixture until the solution is supersaturated, typically 10–30 grams/gal of benzoyl peroxide. Also, notably, the bleaching agent of Step C combined with the Step A, the fixing agent and intermediate mixture, without the addition of Step B, the coloring agent. Additionally, the bleaching agent, provided in a diluted liquid form, may be use d without combination of Step A and Step B to provide some coloration inasmuch as a lightening and improvement in skin color may result from its use alone.

Certain modifications and improvements will occur to those skilled in the art upon a reading of the foregoing description. All modifications and improvements have been deleted herein for the sake of conciseness and readability but are properly within the scope of the following claims.

I claim:

1. An anti-jaundice composition for providing coloration to a corpse, consisting essentially of a bleaching agent, which is stored at room temperature and optionally a fixing agent; wherein the bleaching agent is a peroxide and wherein the fixing agent is selected from the group consisting of formaldehyde, phenol, methanol and combinations thereof.

2. An anti-jaundice composition, for providing coloration to a corpse, consisting essentially of a bleaching agent, which is stored at room temperature and a coloring agent which is erythrosin; wherein the bleaching agent is a peroxide.

3. The anti-jaundice composition according to claim 1, wherein the composition is administered internally.

4. The anti-jaundice composition according to claim 1, wherein the bleaching agent is benzoyl peroxide.

5. The anti-jaundice composition according to claim 1, wherein the bleaching agent is hydrogen peroxide.

6. The anti-jaundice composition according to claim 1, wherein the anti-jaundice composition is administered by injection.

7. The anti-jaundice composition according to claim 1, wherein the anti-jaundice composition is administered by intravenously.

8. The anti-jaundice composition according to claim 1, wherein the anti-jaundice composition is administered intramuscularly.

9. The anti-jaundice composition according to claim 1, wherein the anti-jaundice composition is administered subcutaneously.

10. The anti-jaundice composition according to claim 1, wherein the anti-jaundice composition is administered intraarterially.

11. An anti-jaundice composition for providing coloration to a corpse, consisting essentially of a bleaching agent and a fixing agent, mixed and stored at room temperature and administered internally to a corpse for providing uniform, controlled coloration of the skin and tissue and for preventing tissue degradation wherein the bleaching agent is a peroxide and wherein the fixing agent is selected from the group consisting of formaldehyde, phenol, methanol and combinations thereof.

12. The anti-jaundice composition according to claim 11, wherein the bleaching agent is benzoyl peroxide.

13. An anti-jaundice composition, for providing coloration to a corpse, consisting essentially of a bleaching agent, which is stored at room temperature and a coloring agent which is erythrosine; wherein the bleaching agent is a peroxide.

14. A method of providing an anti-jaundice composition for providing coloration to a corpse, consisting essentially of the steps of:

mixing a fixing agent with water at room temperature to form an intermediate mixture;

adding and mixing a coloring agent to the intermediate mixture at room temperature to form a secondary mixture; and adding and mixing a bleaching agent to the secondary mixture at room temperature to form an anti-jaundice composition.

15. A method of providing an anti-jaundice composition for providing coloration to a corpse, consisting essentially of the steps of:

mixing a fixing agent with water at room temperature to form an intermediate mixture;

adding and mixing a coloring agent to the intermediate mixture at room temperature to form a secondary mixture;

adding and mixing a bleaching agent to the secondary mixture at room temperature to form an anti-jaundice composition; and introducing the anti-jaundice composition internally to the corpse.

16. The method according to claim 15, wherein the anti-jaundice composition is injected.

17. An anti-jaundice composition for providing coloration to a corpse, consisting essentially of a bleaching agent; a coloring agent; and a fixing agent, wherein the composition is stored at room temperature for internal administration to the corpse for stabilizing tissues of the corpse and for preventing degradation and restoring color to the corpse without causing a yellowing appearance of the corpse; wherein the bleaching agent is a peroxide; wherein the coloring agent is erythrosine; wherein the fixing agent is selected from the group consisting of formaldehyde, phenol, methanol and combinations thereof.

18. An anti-jaundice composition for providing coloration to a corpse, comprising a bleaching agent, a coloring agent, and a fixing agent, which are mixed and stored at room temperature, and administered internally to a corpse for providing uniform, controlled coloration of the skin and tissue and for preventing tissue degradation; wherein the bleaching agent is benzoil peroxide, the coloring agent is erythrosin, and the fixing agent is selected from the group consisting of formaldehyde, phenol, methanol, and combinations thereof.

19. A method for treating, preparing, and injecting an anti-jaundice composition into a corpse consisting essentially of the steps of:

mixing a fixing agent with water at room temperature to form an intermediate mixture;

adding and mixing a coloring agent to the intermediate mixture at room temperature to form a secondary mixture;

adding and mixing a bleaching agent to the secondary mixture at room temperature to form an anti-jaundice composition; and injecting the secondary mixture into the corpse for stabilizing tissues of the corpse and for preventing degradation and restoring color to the corpse without causing a yellowing appearance of the corpse.

* * * * *